United States Patent [19]

Brufani et al.

[11] 4,200,573

[45] Apr. 29, 1980

[54] DERIVATIVES OF 3-CARBOXYRIFAMYCIN S AND SV AND PROCESS FOR THEIR PREPARATION

[75] Inventors: Mario Brufani, Castelgandolfo; Egidio Marchi, Casalecchio di Reno; Pierfranco Bellomo, Bologna; Giuseppe Mascellani, Monte San Pietro, all of Italy

[73] Assignee: Alfa Farmaceutici, S.p.A., Bologna, Italy

[21] Appl. No.: 968,409

[22] Filed: Dec. 11, 1978

[30] Foreign Application Priority Data

Dec. 20, 1977 [IT] Italy .................................. 3653 A/77

[51] Int. Cl.² ..................... C07D 491/08; A61K 31/33
[52] U.S. Cl. .............................. 260/239.3 P; 424/244; 424/249; 424/267; 424/250; 424/248.54
[58] Field of Search ................................. 260/239.3 P

[56] References Cited

U.S. PATENT DOCUMENTS

| 3,342,810 | 9/1967 | Maggi et al. | 260/239.3 P |
| 3,349,082 | 10/1967 | Maggi et al. | 260/239.3 P |

*Primary Examiner*—John D. Randolph
*Assistant Examiner*—Robert T. Bond
*Attorney, Agent, or Firm*—Stevens, Davis, Miller & Mosher

[57] ABSTRACT

New compounds being derivatives of 3-carboxyrifamycin S and SV are prepared by oxidation of cyanohydrin of 3-formylrifamycin S to 3-(cyanocarbonyl)rifamycin S, condensation with a compound of formula HR (an alcohol, an amine or an substituted hydrazine) and, optionally, reduction of the derivative of 3-carboxyrifamycin S so obtained to the corresponding SV form. Alternatively 3-(cyanocarbonyl)rifamycin S may be converted to the SV form before condensing with the compound HR.

18 Claims, No Drawings

DERIVATIVES OF 3-CARBOXYRIFAMYCIN S AND SV AND PROCESS FOR THEIR PREPARATION

The present invention relates to derivatives of 3-carboxyrifamycin S and SV having antibacterial activity and to the process for their preparation.

The structure of rifamycins S and SV is widely known and therefore in the description of the present invention simplified structural formulae will be used showing only the aromatic part of the molecule.

The derivatives of 3-carboxyrifamycins S and SV of the present invention correspond to the following formulae:

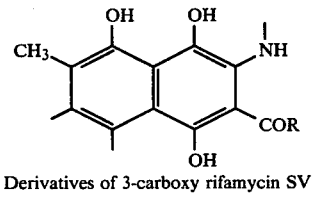

Derivatives of 3-carboxy rifamycin SV

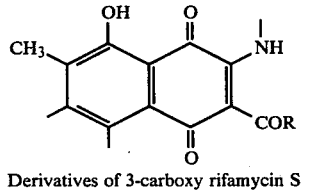

Derivatives of 3-carboxy rifamycin S wherein R represents a CN, a group OR' wherein R' represents an aliphatic group having from 1 to 4 carbon atoms, which may have substituents selected from OH, halogen and lower dialkylamino; R may also represent a group

wherein $R^2$ and $R^3$, equal or different from each other, represent an hydrogen atom, or a $C_1$-$C_4$ aliphatic group, or an aromatic group and may have substituents; $R^2$ and $R^3$ may form together with the nitrogen atom which links them, a 6-member heterocyclic ring, which ring may contain other heteroatoms selected from O and N and may have substituents; R may also represent the group

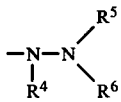

wherein $R^4$ represents an hydrogen atom or a $C_1$-$C_4$ aliphatic group and $R^5$ and $R^6$, equal or different from each other, represent a $C_1$-$C_4$ aliphatic group; $R^4$ and $R^5$ may form, together with the two nitrogen atoms which link them a 6-member heterocyclic ring, which ring may also contain other heteroatoms selected from O and N and may have substituents; $R^5$ and $R^6$ may form together with the nitrogen atom which links them a 6-member heterocyclic ring, which ring may also contain other heteroatoms selected from O and N and have substituents.

The products according to the invention, in their hydroquinonic form (referable to rifamycin SV) are capable of forming alkali metals salts whose solutions are substantially neutral.

Even the quinonic forms (referable to rifamycin S) are capable of forming alkali metals salts when the substituent introduced into the 3 position contains acid groups.

The compounds containing basic substituents may form salts with acids.

Particularly useful are the acids suitable for forming physilogically acceptable salts. Examples of acids are hydrohalogen acids, sulphonic, phosphoric, nitric, perchloric acids, organic carboxylic or sulphonic acid, aliphatic, cycloaliphatic aromatic or heterocyclic acids such as formic, acetic propionic, succinic, glycolic, lactic, malic, tartaric, citric, ascorbic, maleic and hydroxymaleic, piruvic, phenylacetic, benzoic, p-aminobenzoic, anthranilic, p-hydroxybenzoic, salicyclic, p-aminosalicyclic, pamoic, methansulfonic, ethansulfonic, hydroxyethansulfonic, ethylensulfonic, halobenzensulfonic, toluensulfonic, naphthalensulfonic, sulfanilic, methionine, tryptophan, lysine and arginine.

The derivatives of 3-carboxyrifamycins S and SV according to the present invention have an antibacterial activity in vitro as shown by the data in the examples where are reported the minimal inhibiting concentrations (MIC) expressed in mcg/ml against different patogenic microorganisms.

The derivatives according to the present invention may be used for therapeutical purposes and may be administered as such or as salts, for the topical or systemic treatment of infections diseases such as pneumonia, abscesses, furuncolosis, cystitis, cholecystitis, etc.

The products according to the invention, as such or as salts, may be used as drugs in the form of pharmaceutical preparations, together with organic or inorganic, solid or liquid excipients, suitable for the oral, or parenteral administration, or for topical use. Suitable excipients are pharmaceutically acceptable substances which do not interfere with the compounds according to the invention such as water, gelatine, lactose, starch, magnesium stearate, talc, vegetable oils, benzyl alcohol, gums, polyalkylenglycols, vaseline, cholesterol and other known excipients.

The pharmaceutical preparations may be tablets, dragees, capsules, solutions, suspensions, emulsions, ointments and creams. They may contain adjuvants such as preservatives, stabilizers, wetting agents, emulsifiers, solvents and salts to regulate the osmotic pressure or buffers. Subject of the present invention is also the process for the preparation of derivatives of 3-carboxyrifamycin S and SV which process, consists, substantially, in preparing first the 3-(cyanocarbonyl)rifamycin S by oxydation with manganese dioxide of the cyanohydrin of 3-formylrifamycin S. Subsequently the 3-(cyanocarbonyl)rifamycin S (or its SV form) is condensed with a suitable compound of formula H—R (the meanings of R are referred above) to obtain a derivative of 3-carboxyrifamycin S (or, respectively, of the form SV). If so desired it is possible to transform the derivative of 3-carboxyrifamycin S into the form SV by reduction or vice versa by oxydation.

The process according to the invention is based on the observation that the 3-(cyanocarbonyl) derivatives of rifamycin S and SV behave as an active derivative of 3-carboxyrifamycins capable, therefore, of reacting with a number of products to give a series of derivatives of interest as antibiotics.

Such derivatives, on the other hand cannot be prepared starting from 3-carboxyrifamycin which is an instable product and gives very easily rise to reaction of decarboxylation.

According to a more detailed description the preparation process of the 3-carboxyrifamycins S and SV consists in reacting the 3-formylrifamycin SV or its bisulfite adduct, with hydrogen cyanide or with an alkali metal cyanide in order to obtain the 3-(cyanohydroxymethyl)rifamycin SV, in subjecting said 3-(cyanohydroxymethyl)rifamycin SV to oxidation with manganese dioxide to obtain the 3-(cyanocarbonyl)rifamycin S, in condensing said 3-(cyanocarbonyl)rifamycin S with a suitable compound of formula H—R (wherein R has the meanings above indicated, except the meaning CN) to obtain the derivative of 3-carboxyrifamycin S and, if so desired, in transforming said derivative of 3-carboxyrifamycin S into the corresponding derivative of 3-carboxyrifamycin SV by means of mild reducing agents. According to an alternative the preparation process of the derivatives of 3-carboxyrifamycins S and SV consists in transforming said 3-(cyanocarbonyl)rifamycin S into the corresponding 3-(cyanocarbonyl)rifamycin SV by reduction with mild reducing agents, in condensing said 3-(cyanocarbonyl)rifamycin SV with a suitable compound of formula H—R (wherein R has the meanings above indicated except the meaning CN) to obtain the derivative of 3-carboxyrifamycin SV and, if so desired, in transforming said derivative of 3-carboxyrifamycin SV into the corresponding derivative of 3-carboxyrifamycin S by oxidation with mild oxidizing agents.

The process according to the invention can be represented by the following reactions:

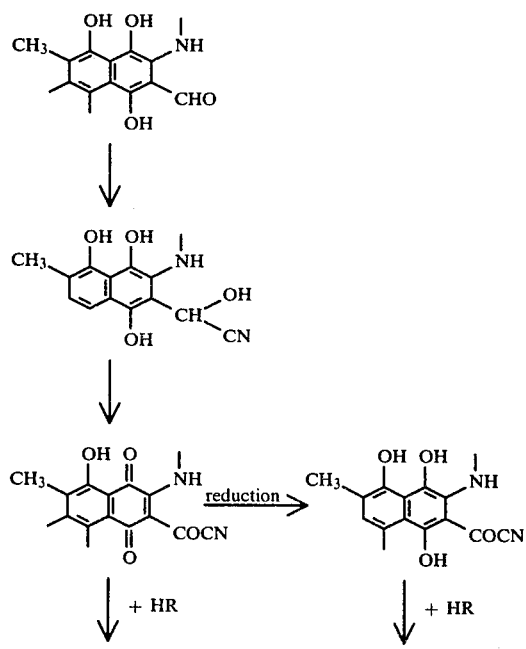

-continued

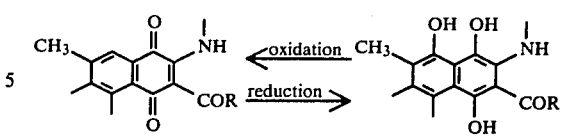

The reaction of 3-formylrifamycin SV with hydrogen cyanide or with alkali metal cyanides, is usually carried out with an excess of sodium or potassium cyanide, preferably in the presence of at least catalytic amounts of an acid such as f.i. acetic acid.

The reaction temperature is usually within the range of from $+5°$ C. to the room temperature. One works in the presence of solvents, preferably hydrophillic ones, capable of dissolving at least in part, the alkali metal cyanide. The preferred solvents are: methanol, ethanol, isopropanol, dioxane, acetonitrile. The cyanuration reaction may also be carried out on the bisulfite adduct of 3-formylrifamycin SV. In such a case it is not necessary to isolate the bisulfite adduct and the reaction may be carried out on the reaction mixture within which the bisulfite adduct has been formed. It has been observed that in the cyanuration reaction of 3-formylrifamycin SV two products are formed the chemical and physicochemical characteristics of which, though being very similar under certain aspects, show some significant differences.

For instance they show on TLC a different Rf.

Keeping in mind that the structure of 3-(cyanohydroxymethyl)rifamycin SV contains, linked to the 3 position an asymmetrical carbon atom, two compounds can be forseen having different configuration of these carbon atoms, which could correspond, hypothetically, to the two compounds which are recovered at the end of the reaction.

The oxidation reaction of 3-(cyanohydroxymethyl)-rifamycin SV is carried out by treating it with manganese dioxide. Although other forms of manganese dioxide give good results, it is preferred to work with manganese dioxide prepared according to the method of Rosenkranz (O. Mancera, C. Rosenkranz, F. Soudheimer, J. Chem. Soc. 2189 (1953)), which presents the advantage of giving higher yields with substantially lower reaction times.

One works in the presence of organic solvents inert and aprotic. The preferred solvents are: chloroform, acetonitrile, ethylacetate. The reaction temperature is above the room temperature.

Usually it is preferred to work at a temperature comprised between the room temperature and the boiling temperature of the solvent.

Although it is possible to isolate, at the end of the reaction, the 3-(cyanocarbonyl)rifamycin in the S form, it is preferred to use this product directly for the subsequent condensation reaction. When working according to the above mentioned alternative it is necessary to transform said 3-(cyanocarbonyl)rifamycin S into the corresponding form hydroquinonic, that is in the 3-(cyanocarbonyl)rifamycin SV.

This can be carried out by submitting the 3-(cyanocarbonyl)rifamycin S to mild reaction by means of reducing agents. The preferred reducing agents are ascorbic acid and sulfur dioxide.

The reaction is carried out in solvents such as acetonitrile and dioxane and using, for instance, a saturated solution of ascorbic acid in acetonitrile, or in dioxane. It is possible to work also in the presence of water or organic solvents containing water. In such cases however it is convenient to avoid a long staying in the aqueous reaction medium. It has been in fact observed that the presence of water for prolonged times leads to the formation of 3-carboxyrifamycin which is an unstable product which easily decomposes, lowering, consequently, the yields in the desired products.

The condensation reaction with the compound H—R can be carried out either starting from 3-(cyanocarbonyl)rifamycin S or from the corresponding form SV according to the two above mentioned alternatives. It has been however observed that the yields in the desired products can vary according to the nature of the compound H—R. Thus when HR is a secondary amine, or an alcohol or a trisubstituted hydrazine the best results, in term of yield and of purity of the products, are reached starting from the 3-(cyanocarbonyl)rifamycin S, whereas when HR is a primary amine or a hydrazine bearing a free $NH_2$ better results are obtained starting from the 3-(cyanocarbonyl)rifamycin SV.

In any case one works in the presence of inert solvents. The preferred solvent is dioxane.

In the case HR is an amine or a hydrazine from 1 to 4 moles of such products per mole of 3-(cyanocarbonyl)rifamycin are used.

The preferred molar ration is 2:1.

In the case of amines the reaction temperature is between 0° C. and the room temperature.

In the case of scarsely reactive amines or hydrazines having the $NH_2$ free it is possible to work also at higher temperatures such as for instance 50°-60° C.

In the case HR is an alcohol an excess thereof is used to that is acts as a co-solvent together with the solvent used to bring the 3-(cyanocarbonyl)rifamycin in solution. The reaction temperature, in the case of alcohols is between the room temperature and 60°-70° C.

The derivatives of 3-carboxyrifamycin S can be easily transformed into the corresponding derivatives of rifamycin SV by reduction with usual reducing agents such as sodium hydrosulfite, sodium thiosulfate, sulfur dioxide and particularly ascorbic acid.

The derivatives of rifamycin SV can be easily transformed into the corresponding derivatives of rifamycin S by oxidation by means of the known oxidizing agents for the oxidation of hydroquinones to quinones, such as ammonium persulfate, potassium ferricyanide, ferric chloride, hydrogen peroxide, oxygen of air and, particularly, manganese dioxide.

The following examples are given to illustrate the invention.

The thin layer chromatographies (TLC) referred therein have been performed on silica gel layers 60 $F_{254}$ thickness 0.2 mm an aluminium plants (Merck).

The composition of eluents are expressed in v/v.

The Rf values are indicated as $Rf_F$=referred to the Rf of 3-formylrifamycin SV $Rf_S$=referred to the Rf of rifamycin S.

In the UV spectra the wave lengths are expressed in nm and the absorptions, in brackets, as log ε.

In the IR spectra the values are expressed in $cm^{-1}$.

The NMR spectra have been carried out at 60 MHz in $CDCl_3$, using TMS as a reference. The δ values are in p.p.m.

EXAMPLE 1

Preparation of 3-(cyanohydroxymethyl)rifamycin SV g 0.2 (4 m moles) of sodium cyanide are suspended in 10 ml acetonitrile containing a trace of acetic acid.

After 10 minutes g 1 of 3-formylrifamycin SV (1.38 m. moles) are added gradually and the mass is stirred for 3 hours at room temperature.

The reaction product gives on TLC (chloroform/methanol/acetic acid=88/12/1) two yellow spots with $Rf_F$=0.4 and 0.6, 20 ml. 10% aqueous citric acid are added and the solution is washed repeatedly with chloroform.

The organic phase, after repeated washings with water is dried and brought to dryness. The residue is dissolved by heating in ethylformiate and on cooling g 0.463 (yield 45%) of 3-(cyanohydroxymethyl)rifamycin SV crystallize, corresponding to the product at Rfhd F=0.4.

The ethylformiate liquor mother is brought to dryness and the residue dissolved by heating in ethylacetate.

On cooling g 0.360 (yield 35%) of product corresponding to $Rf_F$=0.6 crystallize.

It is presumed that the last mentioned product is a stereoisomer of the above.

| Analysis: | C % | H % | N % |
|---|---|---|---|
| 3-(cyanohydroxymethyl) rifamycin SV | 62,41 | 7,08 | 3,64 |
| Product with $Rf_F$ = 0,6 | 60,97 | 6,55 | 3,53 |
| Calculated for $C_{39}H_{48}N_2O_{13}$ | 62,22 | 6,43 | 3,72 |

UV Spectra in methanol: 3-(cyanohydroxymethyl)rifamycin SV: 447 (4.16), 314 (4.27), 228 (4.59). Product with $Rf_F$=0.6: 447 (4.11), 314 (4.20), 228 (4.58).

IR Spectra in chloroform: 3-(cyanohydroxymethyl)rifamycin SV: 3440 (m), 3100 (m), 2970 (m), 2930 (m), 2870 (m), 2830 (m), 1720 (strong), 1715 (s), 1655 (m), 1635 (m), 1610 (weak). Product with $Rf_F$=0.6: 3620 (w), 3460 (m), 3300 (broad), 2980 (m), 2930 (m), 2880 (m), 2730 (w), 1725 (s), 1655 (m), 1650 (m), 1635 (m), 1610 (w).

NMR Spectra: 3-(cyanohydroxymethyl)rifamycin SV: 0.12 (d), 0.6 (d), 0.84 (d), 1.05 (d), 1.85 (s), 2.1 (s), 2.24 (s), 3.50–4.10 (m), 4.70–5.40 (m), 5.90–6.70 (m), 9.64 (s), 12.30 (s). Product with $Rf_F$=0.6: 0.14 (d), 0.58 (d), 0.90 (m), 1.83 (s), 2.06 (s), 2.10 (s), 2.2 (s), 3.09 (s), 3.5 (s), 4.10 (m), 5.05 (m), 6.10 (m), 10.20 (s), 12.04 (s).

EXAMPLE 2

Preparation of 3-(cyanohydroxymethyl)rifamycin SV mg 725 of 3-formylrifamycin SV (1 m. mole) are added, under stirring to a mixture of 12.5 ml of a molal solution of sodium sulfite and of 2.5 ml of 1 N sulfuric acid. After stirring to complete solution a dark yellow solution is obtained. The bisulfite adduct, contained in the solution shows on TLC (chloroform/methanol/acetic acid 22.5/2.5/0.25) a Rf=0.

mg 75 of sodium cyanide (1.5 m. mole) and 10 ml alcohol are added to the solution under stirring for 4 hours. The recovery and the isolation of the products is carried out as in Example 1.

The overall yield of the two products with $Rf_F$=0.4 and with $Rf_F$=0.6 is 85% of the theory.

EXAMPLE 3

Preparation of 3-(cyanocarbonyl)rifamycin S and SV g 1,5 of manganese dioxide (prepared according to Rosenkranz) are added to g 0.3 of 3-(cyanohydroxymethyl)rifamycin Sv dissolved in 80 ml acetonitrile.

After stirring at room temperature for 40 minutes the manganese dioxide is filtered off. The filtrate contains a product light violet having $Rf_S=0.6$ (chloroform/methanol 30/1) the IR spectrum in chloroform shows the following peaks:

3500 (s), 3390 (s), 2980 (m), 2910 (s), 2800 (m), 1725 (s), 1705 (s), 1630 (s), 1595 (s), etc.

The filtrate is treated with a saturated solution of L(+) ascorbic acid in 10 ml acetonitrile. The solution contains a brick-red stable product with a $Rf_F=0.34$ (chloroform/methanol 43/7).

The solution is concentrated under vacuum to a third of the original volume, the residue is dissolved in chloroform and the organic solution is washed twice with water, dried and brought to dryness.

The residue is purified by passing it through a column (h=12 cm $\phi=1.5$ cm) of silica gel 60 (70–230 mesh ASTM) using a eluent solvent a mixture chloroform/methanol 43/7. The fractions containing the compound with $Rf_F=0.34$ are collected, combined and brought to dryness (yield 80%).

IR Spectrum in chloroform: 3500 (s), 3450 (w), 3390 (w), 3300 (w), 2990 (s), 2920 (s), 1720 (s), 1700 (s), 1685 (w), 1640 (w), 1600 (s), etc.

UV Spectrum in acetonitrile: 477 (3.93), 312 (4.08), 232 (4.44), 218 (4.48).

EXAMPLE 4

One works as in Example 2 except that the oxidation reaction with manganese dioxide is carried out at 60° C. for 25 minutes. The same results are obtained.

EXAMPLE 5

Working as in Example 3 but using chloroform in place of acetonitrile substantially the same results are obtained.

EXAMPLE 6

Preparation of 3-(carbomethoxy)rifamycin S g 0.720 (1 m. mole) of 3-(cyanohydroxymethyl)rifamycin SV are oxidized with manganese dioxide to 3-(cyanocarbonyl) rifamycin S according to Example 3.

The manganese dioxide is filtered off, 50 ml anhydrous methanol are added and the solution is stirred at 50° C. for 15 minutes, brought to dryness and the residue is crystallized from acetonitrile. The 3-(carbomethoxy)rifamycin S is obtained as a yellow product (changing to violet on exposure to the air) which on TLC has a $Rf_S=0.83$ (chloroform/methanol 22/1). Obtained g 0.6 (yield 80% of the theory).

UV Spectrum in methanol: 218 (4.56), 268 (4.34), 318 (4.25), 395 (3.66), 535 (2.78).

IR Spectrum in chloroform: 3400 (m), 3350 (m), 2960 (m), 2930 (m), 2870 (m), 2830 (w), 1735 (s), 1715 (s), 1660 (m), 1640 (m), 1630 (s), 1600 (s).

NMR Spectrum: 0.18 (d), 0.70 (d), 0.91 (d), 1.03 (d), 1.78 (s), 2.09 (s), 2.38 (s), 3.00 (s), 3.20 (s), 3.30–4.00 (m), 3.94 (s), 4.80–5.30 (m), 6.00–7.00 (m), 8.6 (s), 12.6 (s).

| Minimal inhibiting concentration (MIC): | | | |
|---|---|---|---|
| St. Aureus 209 P | Klebsiella Ottaviani | Salmonella p typhi B | E. Coli ML/35 |
| 0,05–0,1 | 25–50 | >50 | 25–50 |

EXAMPLE 7

The same product of the preceeding Example has been obtained substantially with the same results by condensing 3-(cyanocarbonyl)rifamycin SV with methanol and oxidizing subsequently with manganese dioxide the 3-carbomethoxyrifamycin SV to 3-carbomethoxyrifamycin S.

EXAMPLE 8

Preparation of 3-(N-methyl N'-piperazinylcarbonyl)rifamycin S 0.6 ml (5.3 m. mole) of N-methylpiperazine are added to g 2 (2.65 m. mole) of 3-(cyanocarbonyl)rifamycin SV in 100 ml anhudrous dioxane. After stirring at room temperature for 15 minutes, g 3 of manganese dioxide prepared according to Rosenkranz are added.

After filtering the solution is concentrated to one third of the volume, diluted with chloroform and washed with water to neutrality, dried, brought to dryness and the residue is crystallized from acetonitrile.

Violet product (yellow in chloroform) having Rf=0.6 (with reference to the Rf of 3-(cyanocarbonyl)rifamycin S (chloroform/methanol 23/2). Yield g 1 (46% of the theory).

| Elemental analysis: | C % | H % | N % |
|---|---|---|---|
| Found | 59,74 | 6,70 | 4,97 |
| Calculated for $C_{43}H_{55}N_3O_{13}$ | 62,83 | 6,74 | 5,11 |

IR Spectrum in chloroform: 3460 (m), 3370 (m), 2960 (s), 2930 (s), 2800 (w), 1740 (s), 1710 (s), 1655 (s), 1630 (s), 1595 (s).

NMR Spectrum: 0.12 (d), 0.62 (d), 0.90 (d), 1.02 (d), 1.78 (s), 2.02 (s), 2.10 (s), 2.32 (s), 2.42 (s), 2.66 (m), 3.14 (s), 3.54 (m), 3.90–4.20 (m), 4.80–5.30 (m), 6.00–7.10 (m), 8.50 (s).

| MIC: | | | |
|---|---|---|---|
| St. Aureus 209 P | Klebsiella Ottaviani | Salmonella p typhi B | E. Coli ML/35 |
| 0,1–0,25 | >50 | >50 | >50 |

EXAMPLE 9

The 3-(N-methyl, N'-piperazinylcarbonyl)rifamycin S has been obtained in yield lower then that of the preceeding Example, by condensing directly the N-methylpiperazine with 3-(cyanocarbonyl)rifamycin S.

EXAMPLE 10

Preparation of 3-(NN-dimethyl N-hydrazinocarbonyl)rifamycin S 2 ml of NN-dimethylhydrazine are added portionwise to g 2 of 3-(cyanocarbonyl)rifamycin SV (2.65 m. mole) dissolved in 100 ml dioxane. The solution is stirred at room temperature for 1 hour. The mixture contains a gold yellow product which on TLC shows a Rf=0 (chloroform/methanol) 43/7. g 3 of manganese dioxide are added. After stirring at room temperature for 15 minutes, filtering, addition of chloroform, repeated washings with water, drying and bringing to dryness, the residue is purified in a chromatographic column ($\phi=2.5$, h=25 cm) of silica gel 60 (70–230 mesh ASTM) using as eluent solvent the mixture: chloroform/methanol/acetic acid 22.5/2.5/0.25.

The brown violet fractions having $Rf_S=0.65$ (same eluent as above) are combined and evaporated to one third of the volume.

After adding chloroform, washing with water, drying and bringing to dryness the residue is dissolved in chloroform and precipitated with n-hexane.

IR Spectrum in $CHCl_3$: 3450 (m), 2900 (m), 2920 (m), 2860 (m), 1730 (s), 1700 (s), 1640 (s), 1630 (s), 1595 (s).

| MIC: | | | |
|---|---|---|---|
| St. Aureus 209 P | Klebsiella Ottaviani | Salmonella p typhi B | E. Coli ML/35 |
| <0,005 | >50 | >50 | >50 |

EXAMPLE 11

Preparation of 3-(p.bromoanilinocarbonyl)rifamycin S g 1 (1.3 m. mole) of 3-(cyanocarbonyl)rifamycin S is prepared according to Example 3 and to the reaction mixture are added mg 400 (2.32 m. mole) of 4-bromoaniline.

After 2 hours of stirring at room temperature the solution is concentrated under vacuum to small volume, 100 ml chloroform are added the solution is washed repeatedly with water containing a small amount of hydrochloric acid and is brought to dryness.

The product, light brown, is purified by preparative TLC chromatography on silica gel 60 $F_{254}$, thickness 2 mm on aluminum plates, using as solvent and eluent chloroform/methanol 22.5/2.5 Rf=0.9.

The product is precipitated from ethylacetate with n-hexane. Yield 400 mg (34%).

IR Spectrum in chloroform: 3460 (m), 3350 (m), 2950 (m), 2920 (m), 2865 (m), 1740 (s), 1710 (s), 1865 (s), 1365 (s), 1605 (s).

NMR Spectrum: 0–1.20 (m), 1.82 (s), 2.10 (2 s), 2.55 (s), 3.15 (s), 4–7 (m), 7.6 (2 d).

EXAMPLE 12

Preparation of 3-(1 glyceroxycarbonyl)rifamycin S 750 mg of 3-(cyanohydroxymethyl)rifamycin SV are oxidized according to Example 3; after filtration from manganese dioxide 10 ml of glycerin-alfa-beta-isopropylidenether (Beilst XIX 65 (1934)) are added.

After 2 hours of stirring the solution is concentrated to small volume, 100 ml ethylacetate added, washed repeatedly with water and brought to dryness.

The acetonide protection in the glyceryl chain is removed by treating 500 mg of the product dissolved in 25 ml dioxane with 15 ml sulfuric acid 20% for 4 hours. Overall yield 400 mg (49% of theory).

| Elemental analysis: | C % | H % | N % |
|---|---|---|---|
| Found | 59,33 | 6,53 | 1,77 |
| Calculated for $C_{41}H_{51}NO_{16}$ | 60,50 | 6,32 | 1,72 |

IR Spectrum in chloroform: 3460, 3350, 2990, 2960, 2930, 2875, 1740 (s), 1710 (s), 1660 (w), 1640 (m), 1625 (s), 1600 (s).

| MIC: | | | |
|---|---|---|---|
| St. Aureus 209 P | Klebsiella Ottaviani | Salmonella p typhi B | E. Coli ML/35 |
| ≈0,5 | >100 | >100 | >100 |

EXAMPLE 13

Preparation of 3-(N,N dimethylaminocarbonyl)rifamycin S

One works as in Example 12. After filtration of the manganese dioxide ml 5 of a saturated solution of dimethylamine in tetrahydrofuran are added. After 15 minutes of reaction at 40° C. in closed vessel, the solution is brought to dryness and the residue is purified by preparative TLC. The solvent used is a mixture chloroform/methanol=23/2. mg 500 (73% of theory) of a product brown - violet are obtained. $Rf_F=2.0$ eluent: chloroform/methanol/acetic acid=22.5/2,5/0.25.

IR Spectrum in KBr: 3450 (s), 2970 (m), 2935 (m), 2880 (m), 1740 (s), 1710 (s), 1670 (m), 1660 (m), 1635 (s), 1600 (s).

UV Spectrum: 213 (4,57), 272 (4,37), 308 (4,22), 400 (3,62), 530 (2,61).

NMR Spectrum: 0.15 (d), 0.6–1.1 (m), 1.78 (s), 2.02 (s), 2.07 (s), 2.32 (s), 3–3.1 (m), 3.4–7.0 (m), 8,25 (broad).

| MIC: | | | |
|---|---|---|---|
| St. Aureus 209 P | Klebsiella Ottaviani | Salmonella p typhi B | E. Coli ML/35 |
| 0,05–0,025 | >50 | >50 | >50 |

EXAMPLE 14

Preparation of 3-((N-(N'-piperidinyl)N-methyl)aminocarbonyl)rifamycin S 600 mg (0.80 m. mole) of 3-(cyanocarbonyl)rifamycin S are prepared according to Example 3. After filtering off the manganese dioxide mg 500 (4.38 m. mole) of N-(methylamino) piperidine are added. After two days of stirring at room temperature 300 mg of manganese dioxide are added and the suspension stirred for 15 minutes. The manganese dioxide is filtered off, the solution brought to dryness and the residue purified by preparative TLC. The solvent used is a mixture chloroform/methanol=23/2. Obtained mg 200 (yield 30% of theory) of a light violet product having $Rf_S=0.67$ (chloroform/ethanol 24/1).

IR Spectrum in chloroform: 3435 (m), 3345 (m), 2970 (w), 2910 (s), 2840 (w), 1735 (m), 1720 (s), 1700 (s), 1655 (m), 1625 (s), 1595 (s).

| MIC: | | | |
|---|---|---|---|
| St. Aureus 209 P | Klebsiella Ottaviani | Salmonella p typhi B | E. Coli ML/35 |
| ≈0,03 | >50 | >50 | >50 |

We claim:

1. A derivative of 3-carboxyrifamycin S or SV of the formula:

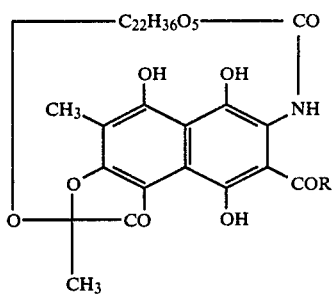

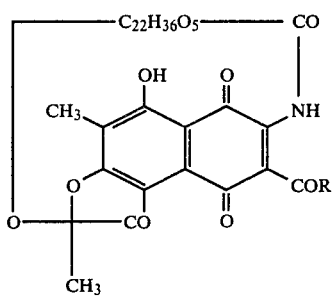

wherein R represents a CN, a group OR' wherein R' represents a saturated aliphatic group having from 1 to 4 carbon atoms which may have substituents selected from OH, halogen and lower dialkylamino; R may also represent a group

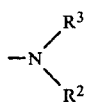

wherein $R^2$ and $R^3$, equal or different from each other, represent an hydrogen atom, or a $C_1$-$C_4$ saturated aliphatic group or an aromatic group with 4 to 6 C atoms and may be substituted by bromine or by an amino group; $R^2$ and $R^3$ may form, together with the nitrogen atom which links them, a 6-member heterocyclic ring, which ring may contain 1 to 2 other heteroatoms selected from O and N; R may also represent the group

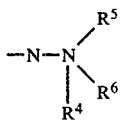

wherein $R^4$ represents an hydrogen atom or a $C_1$-$C_4$ saturated aliphatic group and $R^5$ and $R^6$, equal or different from each other, represent a $C_1$-$C_4$ saturated aliphatic group; $R^4$ and $R^5$ may form, together with the two nitrogen atoms, which link them, a 6-member heterocyclic ring; $R^5$ and $R^6$ may form, together with the nitrogen atom which links them, a 6-member heterocyclic ring, which ring may also contain other heteroatoms selected from O and N and have substituents.

2. 3-(cyanocarbonyl)rifamycins S and SV.
3. 3-(carbomethoxy)rifamycin S.
4. 3-(N-methyl, N'-piperazinylcarbonyl)rifamycin S.
5. 3-(N,N dimethyl N'-hydrazinocarbonyl)rifamycin S.
6. 3-(p.bromoanilinocarbonyl)rifamycin S.
7. 3-(1 glyceroxycarbonyl)rifamycin S.
8. 3-(N,N dimethylaminocarbonyl)rifamycin S.
9. 3-((N-(N'-piperidinyl)N-methyl)aminocarbonyl)rifamycin S.

10. Process for the preparation of a derivative according to claim 1 consisting in reacting the 3-formylrifamycin SV or its bisulfite adduct, with hydrogen cyanide or with an alkali metal cyanide to obtain the 3-(cyanohydroxymethyl)rifamycin SV, in subjecting said 3-(cyanohydroxymethyl)rifamycin SV to oxidation with manganese dioxide to obtain the 3-(cyanocarbonyl)rifamycin S, in condensing said 3-(cyanocarbonyl)rifamycin S with a suitable compound of formula H—R (wherein R has any of the meanings above indicated, except for CN) to obtain the derivative of 3-carboxyrifamycin S and, if so desired, in transforming said derivative of 3-carboxyrifamycin S into the corresponding derivative of 3-carboxyrifamycin SV, by means of mild reducing agents.

11. Process for the preparation of a derivative according to claim 1 consisting in reacting the 3-formylrifamycin SV or its bisulfite adduct with hydrogen cyanide or with an alkali metal cyanide to obtain the 3-(cyanohydroxymethyl)rifamycin SV, in subjecting said 3-(cyanohydroxymethyl)rifamycin SV to oxidation with manganese dioxide to obtain the 3-(cyanocarbonyl)rifamycin S, in converting said 3-(cyanocarbonyl)rifamycin S into the corresponding 3-(cyanocarbonyl)rifamycin SV to reduction with mild reducing agents, in condensing said 3-(cyanocarbonyl)rifamycin SV with a suitable compound of formula HR (wherein R has any of the meanings above indicated except for CN) to obtain the derivative of 3-carboxyrifamycin SV and, if so desired, in transforming said derivative of 3-carboxyrifamycin SV into the corresponding derivative of 3-carboxyrifamycin S, by oxidation with mild oxidizing agents.

12. Process according to one of claims 10 and 11 wherein the reaction of 3-formylrifamycin SV or its bisulfite adduct is carried out with an excess of sodium or potassium cyanide, in the presence of at least a catalytic amount of an acid at a temperature comprised between 5° C. and the room temperature in the presence of preferably hydrophilic solvents.

13. Process according to one of claims 10 and 11 wherein the oxidation of 3-(cyanohydroxymethyl)rifamycin SV to 3-(cyanocarbonyl)rifamycin S is carried out by treatment with manganese dioxide, in the presence of inert and aprotic solvents, at a temperature above the room temperature.

14. Process according to claim 11 wherein the conversion of 3-(cyanocarbonyl)rifamycin S to 3-(cyanocarbonyl) rifamycin SV is carried out by reduction with reducing agent such as ascorbic acid, sulfur dioxide in the presence of solvents such as acetonitrile and dioxane.

15. Process according to one of claims 10 and 11 wherein the condensation of 3-(cyanocarbonyl)rifamycins S and SV with the compound HR, when the latter is an amine or an hydrazine is carried out in the presence of inert solvents at temperatures between 0° and 60° C. and using from 1 to 4 moles of said compound per mole of 3-(cyanocarbonyl)rifamycin.

16. Process according to one of claims 10 and 11 wherein the condensation of 3-(cyanocarbonyl)rifamycins S and SV with the compound HR, when the latter is an alcohol is carried out in the presence of inert solvents at temperatures between the room temperature and 70° C. and using an excess of alcohol.

17. Process according to one of claims 10 and 11 wherein said derivatives of 3-carboxyrifamycin S are transformed into the corresponding derivatives of 3-carboxyrifamycin SV by reduction with usual reducing agent such as sodium hydrosulfite, sodium thiosulfate, sulfur dioxide and, particularly ascorbic acid.

18. Process according to one of claims 10 and 11 wherein said derivatives of 3-carboxyrifamycin SV are transformed into the corresponding derivatives of 3-carboxyrifamycin S by means of known oxidizing agents such as ammonium persulfate, potassium ferricyanide, ferric chloride, hydrogen peroxide, oxygen of air and particularly manganese dioxide.

* * * * *

UNITED STATES PATENT AND TRADEMARK OFFICE
CERTIFICATE OF CORRECTION

PATENT NO. : 4,200,573
DATED : Apr. 29, 1980
INVENTOR(S) : Brufani et al.

It is certified that error appears in the above-identified patent and that said Letters Patent are hereby corrected as shown below:

In column 3, the second formula lacks a bond; the correct formula is:

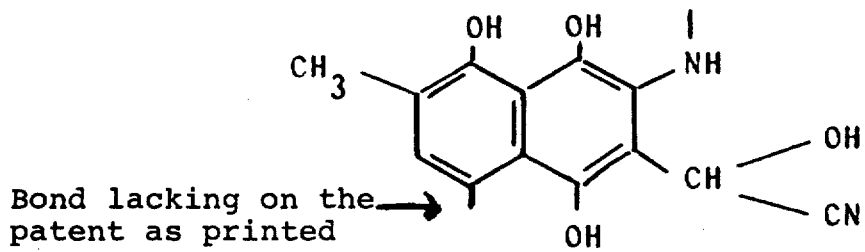

In column 6, line 58, the word "sulfite" must read --bisulfite--.

Signed and Sealed this

First Day of February 1983

[SEAL]

Attest:

GERALD J. MOSSINGHOFF

Attesting Officer

Commissioner of Patents and Trademarks